United States Patent
Bezwada et al.

[11] Patent Number: 6,113,624
[45] Date of Patent: *Sep. 5, 2000

[54] ABSORBABLE ELASTOMERIC POLYMER

[75] Inventors: Rao S. Bezwada, Whitehouse Station; Kevin L. Cooper, Warren, both of N.J.

[73] Assignee: Ethicon, Inc., Somerville, N.J.

[ * ] Notice: This patent is subject to a terminal disclaimer.

[21] Appl. No.: 09/237,542

[22] Filed: Jan. 26, 1999

Related U.S. Application Data

[63] Continuation-in-part of application No. 08/953,931, Oct. 20, 1997, Pat. No. 5,868,788, which is a continuation of application No. 08/665,156, Jun. 14, 1996, abandoned, which is a division of application No. 08/537,343, Oct. 2, 1995, Pat. No. 5,639,851.

[51] Int. Cl.[7] ............................................... A61B 17/00
[52] U.S. Cl. ..................... 606/230; 606/151; 606/154; 606/158; 606/209; 606/220; 606/231; 606/233
[58] Field of Search .............................. 606/151, 154, 606/158, 219, 220, 230, 231, 233

[56] References Cited

U.S. PATENT DOCUMENTS 5,868,788  2/1999  Bezwada et al. ....................... 606/230

*Primary Examiner*—Peter A. Szekely

[57] ABSTRACT

Medical devices or components for medical devices formed from bioabsorbable elastomers comprising a segmented copolymer are disclosed. The segmented copolymer is a copolymer of from about 30 to about 40 mole percent of lactide and the balance being substantially p-dioxanone. The segmented copolymers surprisingly exhibit elastomeric properties, and the copolymers are bioabsorbable. The combination of physical and biological properties of these elastomeric copolymers are particularly well suited for numerous medical and surgical applications.

8 Claims, No Drawings

ABSORBABLE ELASTOMERIC POLYMER

The present invention is a continuation-in-part of patent application Ser. No. 08/953,931, filed Oct. 20, 1997 now U.S. Pat. No. 5,868788, which is a continuation of patent application Ser. No. 08/665,156, filed Jun. 14, 1996 now abandoned, which is a divisional of patent application 08/537,343, filed Oct. 2, 1995 now U.S. Pat. No. 5,639,851 (all hereby incorporated by reference).

FIELD OF THE INVENTION

This invention relates to absorbable elastomer copolymers and more particularly to biocompatible absorbable elastomers of lactide and p-dioxanone that may be used in medical devices.

BACKGROUND OF THE INVENTION

This invention relates to medical devices or components for such devices. More specifically, it relates to bioabsorbable elastomers fabricated into devices or components for devices suitable for medical applications.

The desirability of elastomeric materials for medical applications has been well established. For example, Thermoplast. Elastomers 3, Pap. Two-Day Semin., 3rd, pp. 68–71(1991) discloses the fabrication of films and sheeting from copolyester elastomers for medical applications. These films can be used as transdermal patches for delivering bioactive agents through the surface of the skin, surgical wound dressings, I.V. site dressings, ostomy site dressings, and operating room garments. The copolyester elastomers are polymers with "hard" and "soft" segments. Their properties, such as flexibility, elasticity, and resistance to creep, can be tailored by varying the ratio of the hard and soft segments in the copolyester.

In addition to certain copolyesters, which have elastomeric properties suitable for medical applications, polyurethane elastomers have also found acceptance within the medical community for numerous applications. This acceptance has led to the availability of TECOFLEX® Aliphatic Polyurethanes for medical device applications. These elastomeric polyurethanes are prepared by reacting methylene bis(cyclohexyl) diisocyanate with poly(tetramethylene ether glycol). Some of the devices fabricated from these materials are intended primarily for implantation into the body. See the advertising brochure for TECOFLEX® Medical Grade Aliphatic Thermoplastic Polyurethanes from Thermedics, Inc.

While the commercial viability of elastomeric polymers for medical applications has been established, a need exists in the medical profession for certain properties which have not been met by the elastomeric polymers described above. For numerous applications, especially for those applications requiring a surgical device which is to be implanted in bodily tissue, the polymer from which the device is prepared must be bioabsorbable. In other words, the device must be capable of breaking down into small, non-toxic segments which can be metabolized or eliminated from the body without harm.

Unfortunately, although the elastomeric polymers described in the preceding references exhibit the requisite biocompatability, strength and processability, for numerous medical device applications, such elastomeric polymers are not absorbable in bodily tissue. Since these polymers are nonabsorbable in bodily tissue, surgical implants made from these elastomeric polymers would remain indefinitely within the bodily tissue, possibly causing adverse tissue reaction or other complications associated with the confinement of foreign matter in bodily tissue.

A large body of art has been created over many years, which focuses on the use of bioabsorbable polymers for numerous medical and surgical applications. As an example of this, the reader can review U.S. Pat. Nos. 5,133,739, 4,788,979 and 4,605,730. These patents teach the preparation of certain copolymer compositions of $\epsilon$-caprolactone and glycolide for specific bioabsorbable medical applications. The copolymer compositions are described as particularly useful for the preparation of filaments suitable for use as sutures, and for use as coating compositions for coating the surface of sutures to improve tiedown properties. Although the copolymer compositions described in these references exhibit a combination of outstanding biological and physical properties which make such polymer compositions particularly well adapted for numerous surgical applications, such polymer compositions do not exhibit a desirable degree of elasticity. Therefore, these copolymers would not be desirable for use in medical applications requiring elastomeric properties.

A partial answer to the problem of developing elastomeric copolymers, which are biocompatible, and bioabsorbable in bodily tissue has been suggested in the art. Griipma et al., Polymer Bulletin 25, 327–333 (1991), describes a 50/50 mole per mole copolymer of L-lactide and $\epsilon$-caprolactone. The copolymer is said to be elastomeric, and it degrades into non-toxic segments, so it is said to be useful for biomedical applications such as nerve guides. Similarly, U.S. Pat. Nos. 4,045,418 and 4,057,537 describe copolymers prepared from 75–85 parts by mole D,L-lactide and 25–15 parts of $\epsilon$-caprolactone. The copolymers are stated to be easily moldable, thermoplastic elastomers, which are biodegradable to harmless substances. Additionally, the copolymers can be modified by replacing a portion of the lactide with glycolide, and thus preparing a terpolymer of lactide/glycolide/$\epsilon$-caprolactone containing predominantly lactide.

While the elastomeric copolymers of lactide and $\epsilon$-caprolactone have addressed the needs for certain medical device applications, such copolymers have a major drawback which has prevented their widespread use. Although, the copolymers can be literally interpreted to be "bioabsorbable", the rate of absorption is so slow that it renders the copolymers practically useless for numerous medical applications. This is so because the predominant component of the copolymer, which is poly(lactide), absorbs very slowly in bodily tissue. The other primary component of the copolymer, poly(caprolactone), absorbs even slower. In addition, lactide polymerizes faster than $\epsilon$-caprolactone at 1100° C. so that when the copolymer is made, a segmented copolymer containing long segments of poly(lactide) spaced between segments of poly(caprolactone) is produced. The segmented structure of the copolymer further lowers its bioabsorption rate. All of these factors create a copolymer whose components and morphology do not lend themselves to acceptable bioabsorption rates for numerous medical applications.

In view of the deficiencies of the prior art, it would be highly desirable if medical devices or components for these devices could be fabricated from biocompatible polymers which exhibit the highly desired property of elasticity, without sacrificing mechanical properties, and yet also exhibit a rate of bioabsorbability which is fast enough for numerous medical device applications.

SUMMARY OF THE INVENTION

The invention is a medical device or part thereof formed from a bioabsorbable elastomer. The elastomer comprises a segmented copolymer of from about 30 to about 40 mole percent of lactide, the remainder of the copolymer being substantially p-dioxanone.

This segmented copolymer exhibits the properties of a bioabsorbable elastomer when it is processed to form a medical device or a component of a medical device. This elastomer exhibits not only outstanding physical properties highly desired for elastomeric materials, but also bioabsorbability at a rate which accomplishes essentially complete bioabsorption within a reasonable time period. This is a necessary attribute for numerous medical applications. In preferred embodiments, the medical device or part of such device formed from the bioabsorbable elastomer has a high percent elongation, a low modulus, and outstanding tensile strength. These properties are achieved without sacrificing the bioabsorbability of the elastomeric polymer.

Unlike the elastomeric copolymers containing predominantly segments of polylactide, the segmented copolymers which form the medical devices of this invention exhibit a rate of bioabsorption which is fast enough for numerous medical applications.

The bioabsorbable elastomer can be formed into numerous medical and surgical devices, or components for such devices. For example, the elastomers can be fabricated to form elastomeric foams, tissue scaffolds, sutures, or as components of surgical clips and staples.

DETAILED DESCRIPTION OF THE INVENTION

For purposes of defining this invention, an "elastomer" is defined as a material, which at room temperature can be stretched repeatedly to at least twice its original length and, upon immediate release of the stress, will return with force to its approximate original length. Preferably, the elastomer exhibits a high percent elongation and a low modulus, while possessing good tensile strength and good recovery characteristics. In the preferred embodiments of this invention, the elastomer from which the medical device or component of the device is formed exhibits a percent elongation greater than about 200 preferably greater than about 400. It will also exhibit a modulus (Young's Modulus) of less than about 40,000 psi, preferably less than about 20,000 psi. These properties, which measure the degree of elasticity of the bioabsorbable elastomer, are achieved while maintaining a tensile strength greater than about 500 psi, preferably greater than about 1,000 psi, and a tear strength of greater than about 50 lbs/inch, preferably greater than about 80 lbs/inch.

The term "bioabsorbable" is defined as a class of materials which readily degrade upon exposure to an aqueous environment for a relatively short period of time. Complete bioabsorption should take place within twelve months, although preferably bioabsorption will be complete within nine months and most preferably within six months. In this manner, the elastomer can be fabricated into medical and surgical devices which are useful for a vast array of applications requiring complete absorption within a relatively short time.

The biological properties of the bioabsorbable elastomer used to form the device or part thereof, as measured by its absorption rate and its breaking strength retention in vivo (BSR), can be varied to suit the needs of the particular application for which the fabricated medical device or component is intended. This can be conveniently accomplished by varying the ratio of components of the elastomeric copolymer chosen.

The process of the present invention is a two-step, one-reaction vessel, two-temperature process in which a mixture of p-dioxanone monomer and p-dioxanone homopolymer, is formed at low temperatures of from about 100° C. to about 130° C., preferably 110° C. The mixture is then reacted with lactide at temperatures from about 120° C. to about 190° C. to form copolymers in which segments or sequences are composed of both p-dioxanone and lactide repeating units. These segmented copolymers are, surprisingly and unexpectedly, substantially less crystalline than the block or graft copolymers previously known in the art and, therefore, yield materials with good strength, but shorter BSR (Breaking Strength Retention) profiles, faster absorption rates, much longer elongations and lower stiffness than the block copolymers.

More specifically, the poly(lactide-co-p-dioxanone) segmented copolymers of the present invention are prepared by a process in which p-dioxanone monomer in the initial monomer feed of the copolymer is reacted at low temperatures from about 100° C. to about 130° C., preferably about 110° C., for a sufficient time effective to cause polymerization, preferably about 4 to about 8 hours, followed by reaction with lactide at higher temperatures of about 120° C. to about 190° C. for a sufficient time effective to cause copolymerization, preferably about 1 to about 4 hours.

The segmented copolymers are desirably prepared by reacting the monomers with an initiator such as a mono- or polyhydric alcohol, e.g. diethylene glycol, trimethylol propane, or pentaerythritol; or a hydroxy acid such as lactic or glycolic acid. Other initiators which can be used include polyalkylene glycols such as triethylene glycol, and polyhydroxy alkanes such as glycerol, mannitol, glucose, and the like.

The inherent viscosity of the segmented copolymer is desirably from about 0.7 to about 3.5 deciliters per gram (dL/g) and preferably within a range of from about 1.0 to about 3.0 dL/g, as measured in a 0.1 gram per deciliter (g/dL) solution of the polymer in hexafluoroisopropanol (HFIP) at 25° C. If the inherent viscosity is less than about 0.6 dl/g, then the strength properties of the copolymer would most likely be inadequate for numerous medical device applications. If the inherent viscosity were greater than about 4.0 dl/g, then one may encounter significant processing difficulties in the fabrication of medical devices or components for such devices from the copolymers. This may require solution casting techniques to prepare useful products. In addition, the percent crystallinity of the segmented copolymer, as measured by x-ray diffraction, is advantageously less than about 25 percent, preferably less than about 15 percent. If the crystallinity of the copolymer were greater than about 25 percent, then the copolymer would be relatively stiff and non-elastomeric.

The preferred segmented copolymer is a copolymer of lactide (L-,D- and mixtures thereof,) and p-dioxanone. The most preferred segmented copolymer is a copolymer of L-lactide and p-dioxanone. The amount of lactide from which the segmented copolymer is composed is critical to achieve acceptable elastomeric properties in combination with good mechanical properties. The preferred amount is between 30 percent to about 40 mole percent lactide and more preferably about 40 mole percent lactide with the remainder being p-dioxanone. If less than 30 mole percent of lactide is used, then the copolymer would not exhibit elastomeric properties. If the amount of lactide in the segmented copolymer were greater than about 40 mole percent, then the copolymer also will not exhibit elastomeric properties.

Minor amounts of additives or comonomers can be added to the comonomer mixture from which the segmented copolymer is prepared, so long as these additional additives or comonomers do not significantly impact upon the elastomeric properties of the copolymers, or its rate of bioabsorption. For example, it may be desired to add certain components to modify or enhance the properties of the copolymer for specific applications. So long as the amount of lactide in the comonomer mixture lies within the range from about 30 to about 40 mole percent, and the properties of the copolymer are not substantially effected, then such additional components may be used. Of course, the other primary component of the comonomer mixture in addition to para-dioxanone. Therefore, the term "substantially" which appears in the appended claims refers to allowing the incorporation of such minor components in addition to the balance of the copolymer composition being of these comonomers.

Medical devices and components of these devices can be formed from the bioabsorbable elastomers described above using numerous techniques well known in the art. The elastomers can be melt-processed, for example by extrusion to prepare filaments or tubular structures. Alternatively, the copolymers can be injection molded to fabricate intricately designed parts, or compression molded to prepare films. For the details of such melt-processing techniques, see, for example, F. Rodriguez "Principles of Polymer Systems" McGraw Hill, 1970, Chapter 12.

The bioabsorbable elastomers can also be solvent cast to prepare thin films. Solvent casting can be accomplished using conventional methods such as first dissolving the copolymer in a suitable solvent to make a solution, then casting the solution on a glass plate to make a film, and then evaporating the solvent from the cast film. In another processing scheme, the copolymers can be lyophilized to prepare foams. Lyophilization can be accomplished by first dissolving the copolymer in an appropriate solvent, freezing the solution, and then removing the solvent under vacuum. The set of appropriate solvents include p-dioxane. Lyophilization techniques to prepare films are described in Aspects Theoriques Et Industriels De La Lyophilization by Louis Rey, 1964.

In another embodiment of this invention, the elastomers are reinforced with a filler to improve desired properties. For example, the elastomers can be reinforced with absorbable fibers to prepare ultrasoft films which display high tear strength. The fibers may be desirably in the form of a knitted or non-woven mesh, for example Vicryl® (Polyglactin 910) knitted mesh.

The segmented copolymers of the present invention can be melt processed by numerous methods to prepare a vast array of useful devices. These materials can be injection or compression molded to make implantable medical and surgical devices, including wound closure devices. The preferred devices are suture anchor devices, staples, surgical tacks, clips, plates and screws, and adhesion prevention films and hemostatic foam barriers.

Alternatively, the segmented copolymers of the present invention can be extruded to prepare fibers. The filaments thus produced may be fabricated into sutures or ligatures, attached to surgical needles, packaged, and sterilized by known techniques. The materials of the present invention may be spun as multifilament yarn and woven or knitted to form sponges or gauze, (or non-woven sheets may be prepared) or used in conjunction with other molded compressive structures such as prosthetic devices within the body of a human or animal where it is desirable that the structure have high tensile strength and desirable levels of compliance and/or ductility. Useful embodiments include tubes, including branched tubes, for artery, vein or intestinal repair, nerve splicing, tendon splicing, sheets for tying up and supporting damaged surface abrasions, particularly major abrasions, or areas where the skin and underlying tissues are damaged or surgically removed. Especially, suture applications where Monocryl-like, monofilament sutures with excellent tensile properties but longer BSR profiles than Monocryl are needed, most especially in wound fascia closure applications, where longer absorption times would lead to better tissue fixation.

Additionally, the segmented copolymers of the present invention can be molded to form films which, when sterilized, are useful as adhesion prevention barriers. Another alternative processing technique for the copolymers of the present invention includes solvent casting, particularly for those applications where a drug delivery matrix is desired.

Furthermore, the segmented copolymers of the present invention can be processed by conventional techniques to form foams, which are useful as hemostatic barriers, bone substitutes, and tissue scaffolds.

In more detail, the surgical and medical uses of the filaments, films, foams and molded articles of the present invention include, but are not necessarily limited to knitted products, woven or non-woven, and molded products including:

a. burn dressings
b. hernia patches
c. medicated dressings
d. fascial substitutes
e. gauze, fabric, sheet, felt or sponge for liver hemostasis
f. gauze bandages
g. arterial graft or substitutes
h. bandages for skin surfaces
i. burn dressings
j. orthopedic pins, clamps, screws, and plates
k. clips
l. staples
m. hooks, buttons, and snaps
n. bone substitutes
o. needles
p. intrauterine devices
q. draining or testing tubes or capillaries
r. surgical instruments
s. vascular implants or supports
t. vertebral discs
u. extracorporeal tubing for kidney and heart-lung machines
v. artificial skin and others
w. stents
x. suture anchors
y. injectable defect fillers
z. preformed defect fillers
aa. tissue adhesives and sealants
bb. bone waxes
cc. cartilage replacements
dd. hemostatic barriers
ee. tissue scaffolds The following examples illustrate the most preferred embodiments of this invention, and are intended to be merely illustrative without limiting the spirit and scope of the claimed invention.

EXAMPLE 1
Polylactide homopolymer-Control

To a flame dried 250 ml single neck flask 144.13 gm (1.0 mole) L(-) lactide, 0.114 ml (1.2 mmole/mole of total monomer) of diethylene glycol and 0.1212 ml stannous octoate (0.33 molar solution in toluene) were charged and dried under vacuum at room temperature over night. The flask was then fitted with a flame dried mechanical stirrer and an adapter. The reactor was then purged three times before being vented with nitrogen. The reaction mixture was heated to 185° C. under nitrogen, and maintained at this temperature for about 3.5 hours.

The resulting homopolymer was isolated, ground, and dried for 14 hours at 80° C. under vacuum (0.1 mm Hg), followed by 28 hours at 110° C. under vacuum to remove residual monomers. A weight loss of 1.5% was observed. The polymer had an inherent viscosity of 1.56 dl/g in hexafluoroisopropanol (HFIP).

EXAMPLE 2
p-Dioxanone/Lactide @ 40/60

To a flame dried 250 ml two neck flask 40.83 gm (0.40 mole) p-dioxanone, 0.057 ml (0.6 mmole/mole of total monomer) of diethylene glycol and 0.1212 ml stannous octoate (0.33 molar solution in toluene) were charged and dried under vacuum at room temperature over night. The flask was then fitted with a flame dried mechanical stirrer and an adapter. The reactor was then purged three times before being vented with nitrogen. The reaction mixture was heated to 110° C. under nitrogen, and maintained at this temperature for about 5 hours. A sample was taken for characterization and 86.48 gm (0.60 mole) of L(-) lactide was then added to the prepolymer in the reaction flask. The temperature was then raised to 185° C. and maintained 2.5 hours at this temperature.

The copolymer was isolated, ground, and dried for 14 hours at 80° C. under vacuum (0.1 mm Hg), followed by 42 hours at 110° C. under vacuum to remove residual monomers. A weight loss of 16.2% was observed. The copolymer had an inherent viscosity of 1.37 dl/g in HFIP.

EXAMPLE 3
p-Dioxanone/Lactide @ 50/50

To a flame dried 250 ml two neck flask 51.04 gm (0.50 mole) p-dioxanone, 0.057 ml (0.6 mmole/mole of total monomer) of diethylene glycol and 0.1212 ml stannous octoate (0.33 molar solution in toluene) were charged and dried under vacuum at room temperature over night. The flask was then fitted with a flame dried mechanical stirrer and an adapter. The reactor was then purged three times before being vented with nitrogen. The reaction mixture was heated to 110° C. under nitrogen, and maintained at this temperature for about 5 hours. A sample was taken for characterization and 72.06 gm (0.50 mole) of L(-) lactide was then added to the prepolymer in the reaction flask. The temperature was then raised to 185° C. and maintained 2.5 hours at this temperature.

The copolymer was isolated, ground, and dried for 42 hours at 80° C. under vacuum (0.1 mm Hg). A weight loss of 14.2% was observed. The copolymer had an inherent viscosity of 1.39 dl/g in HFIP.

EXAMPLE 4
p-Dioxanone/Lactide @ 60/40

To a flame dried 250 ml two neck flask 61.25 gm (0.60 mole) p-dioxanone, 0.057 ml (0.6 mmole/mole of total monomer) of diethylene glycol and 0.1212 ml stannous octoate (0.33 molar solution in toluene) were charged and dried under vacuum at room temperature over night. The flask was then fitted with a flame dried mechanical stirrer and an adapter. The reactor was then purged three times before being vented with nitrogen. The reaction mixture was heated to 110° C. under nitrogen, and maintained at this temperature for about 5 hours. A sample was taken for characterization and 57.65 gm (0.40 mole) of L(-) lactide was then added to the prepolymer in the reaction flask. The temperature was then raised to 185° C. and maintained 2.5 hours at this temperature.

The copolymer was isolated, ground, and dried for 42 hours at 80° C. under vacuum (0.1 mm Hg). A weight loss of 16.9% was observed. The copolymer had an inherent viscosity of 1.32 dl/g in HFIP.

EXAMPLE 5
p-Dioxanone/Lactide @ 70/30

To a flame dried 250 ml two neck flask 71.46 gm (0.70 mole) p-dioxanone, 0.057 ml (0.6 mmole/mole of total monomer) of diethylene glycol and 0.12 ml stannous octoate (0.33 molar solution in toluene) were charged and dried under vacuum at room temperature over night. The flask was then fitted with a flame dried mechanical stirrer and an adapter. The reactor was then purged three times before being vented with nitrogen. The reaction mixture was heated to 110° C. under nitrogen, and maintained at this temperature for about 5 hours. A sample was taken for characterization and 43.24 gm (0.30 mole) of L(-) lactide was then added to the prepolymer in the reaction flask. The temperature was then raised to 185° C. and maintained 2.5 hours at this temperature.

The copolymer was isolated, ground, and dried for 48 hours at 80° C. under vacuum (0.1 mm Hg). A weight loss of 20% was observed. The copolymer had an inherent viscosity of 1.27 dl/g in HFIP.

EXAMPLE 6
p-Dioxanone/Lactide @ 85/15

To a flame dried 250 ml two neck flask 86.78 gm (0.85 mole) p-dioxanone, 0.038 ml (0.4 mmole/mole of total monomer) of diethylene glycol and 0.101 ml stannous octoate (0.33 molar solution in toluene) were charged and dried under vacuum at room temperature over night. The flask was then fitted with a flame dried mechanical stirrer and an adapter. The reactor was then purged three times before being vented with nitrogen. The reaction mixture was heated to 110° C. under nitrogen, and maintained at this temperature for about 6 hours. A sample was taken for characterization and 21.62 gm (0.15 mole) of L(-) lactide was then added to the prepolymer in the reaction flask. The temperature was then raised to 140° C. and maintained 4 hours at this temperature.

The copolymer was isolated, ground, and dried for 14 hours at 70° C. under vacuum (0.1 mm Hg), followed by 28 hours at 80° C. under vacuum to remove residual monomers. A weight loss of 19.4% was observed. The copolymer had an inherent viscosity of 2.56 dl/g in HFIP.

EXAMPLE 7

Polymeric films were prepared and tested as described in the U.S. Pat. No. 5,468,253.

TABLE 1

Elastomeric Properties of p-Dioxanone/Lactide copolymers

| Example # | 1 | 2 | 3 | 4 | 5 | 6 | 7 |
|---|---|---|---|---|---|---|---|
| Composition (p-dioxanone/lactide) | 00/100 | 40/60 | 50/50 | 60/40 | 70/30 | 85/15 | 100/00 |
| Elastomeric properties | | | | | | | |
| Maximum Load, PSI | 2021 | 8959 | 5129 | 4593 | 5281 | 6220 | 7382 |
| Stress @ ultimate, PSI | 2021 | 8959 | 4224 | 4593 | 5281 | 6220 | 7061 |
| % strain @ ultimate | 3 | 5 | 266 | 505 | 1243 | 750 | 314 |
| Permanent Set, % | 0 | 0 | 133 | 6 | 62 | 117 | 279 |

I claim:

1. A medical device containing a bioabsorbable elastomer wherein the elastomer consists essentially of a segmented copolymer of: a) from about 30 to about 40 mole percent of lactide thereof, and b) the balance of the copolymer being substantially p-dioxanone wherein the segmented copolymer exhibits an inherent viscosity of from about 0.7 dL/g to about 3.5 dL/g.

2. The elastomeric medical device of claim 1 wherein the segmented copolymer is a copolymer of L-lactide and p-dioxanone.

3. The elastomeric medical device of claim 1 wherein the segmented copolymer is a copolymer of about 40 mole percent of lactide and the balance being p-dioxanone.

4. The elastomeric medical device of claim 1 wherein the device is selected from the group consisting of burn dressings, hernia patches, medicated dressings, fascial substitutes, gauze, fabric, sheet, felt, sponges arterial graft or substitutes, pins, clamps, screws, plates, clips, staples, hooks, buttons, snaps, bone substitutes, needles, intrauterine devices, tubes, surgical instruments, vascular implants or supports, vertebral discs, stents, suture anchors, preformed defect fillers, tissue adhesives and sealants, bone waxes, tissue scaffolds, and hemostatic barriers.

5. The elastomeric medical device of claim 1 wherein the device is a foam.

6. The elastomeric medical device of claim 1 wherein the device is a tissue scaffold.

7. The elastomeric medical device of claim 1 wherein the device is a textile.

8. The elastomeric medical device of claim 1 wherein the device is a film.

* * * * *